(12) United States Patent
Hashimoto et al.

(10) Patent No.: US 9,283,147 B2
(45) Date of Patent: Mar. 15, 2016

(54) ENCAPSULATION DEVICE, MEDICAL CAPSULES, AND ENCAPSULATION METHOD

(71) Applicant: Seiko Epson Corporation, Tokyo (JP)

(72) Inventors: Taki Hashimoto, Shirojiri (JP); Yoshiki Fukui, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 158 days.

(21) Appl. No.: 13/630,765

(22) Filed: Sep. 28, 2012

(65) Prior Publication Data

US 2013/0078308 A1 Mar. 28, 2013

(30) Foreign Application Priority Data

Sep. 28, 2011 (JP) ................................. 2011-213190
Sep. 28, 2011 (JP) ................................. 2011-213192
May 23, 2012 (JP) ................................. 2012-117887

(51) Int. Cl.
*A61K 9/50* (2006.01)
*A61J 3/07* (2006.01)
*B01J 13/04* (2006.01)
*B01J 13/20* (2006.01)
*B01J 13/22* (2006.01)

(52) U.S. Cl.
CPC ... *A61J 3/07* (2013.01); *A61K 9/50* (2013.01); *A61K 9/5073* (2013.01); *A61K 9/5089* (2013.01); *B01J 13/04* (2013.01); *B01J 13/206* (2013.01); *B01J 13/22* (2013.01)

(58) Field of Classification Search
None
See application file for complete search history.

(56) References Cited

U.S. PATENT DOCUMENTS

| 5,453,368 | A | 9/1995 | Tresco et al. | |
|---|---|---|---|---|
| 7,524,902 | B2 * | 4/2009 | Patel et al. | 525/391 |
| 2005/0154310 | A1 | 7/2005 | Bruestle | |
| 2005/0154311 | A1 | 7/2005 | Bruestle | |
| 2005/0154312 | A1 | 7/2005 | Bruestle | |
| 2010/0020385 | A1 * | 1/2010 | Yamamoto et al. | 359/296 |

FOREIGN PATENT DOCUMENTS

| JP | 59-011859 | | 1/1984 |
|---|---|---|---|
| JP | 62-266037 | | 11/1987 |
| JP | 64-008978 | | 1/1989 |
| JP | 05-317387 | | 12/1993 |
| JP | 2002-086492 | | 3/2002 |
| JP | 2005-199067 | | 7/2005 |
| JP | 2005-224647 | | 8/2005 |
| JP | 2007-275812 | | 10/2007 |
| JP | 2007275812 A | * | 10/2007 |
| JP | 2013-071079 | | 4/2013 |
| JP | 2013-071081 | | 4/2013 |
| WO | 2011-139602 | | 11/2011 |

* cited by examiner

*Primary Examiner* — H. Sarah Park
(74) *Attorney, Agent, or Firm* — Workman Nydegger

(57) ABSTRACT

An encapsulation device includes: a fluid injection device that injects a first liquid forming a core; a liquid film holder that holds in film form a second liquid forming a shell containing the core; and a liquid contact device that makes the shell in contact with a third liquid, in which the first liquid is injected toward a liquid film of the second liquid retained by the liquid film holder to form a core, the core is wrapped with the second liquid on passing through the liquid film of the second liquid, thereby forming the shell, and the shell is made in contact with the third liquid to induce chemical reaction.

8 Claims, 13 Drawing Sheets

ENCAPSULATION DEVICE, MEDICAL CAPSULES, AND ENCAPSULATION METHOD

BACKGROUND

1. Technical Field

The present invention relates to an encapsulation device, medical capsules, and an encapsulation method.

2. Related Art

Capsules formed by covering a core substance (core) with a film (shell) have been known. Among the capsules, fine capsules having a particle diameter in micrometer order are referred to as microcapsules (or microspheres and gel beads) and have been developed in recent years. Microcapsules may be imparted with various functions by selecting appropriately the materials for forming the core and the shell. For example, a function of protecting the core from the external environment, a function of controlling the rate of releasing the core to the external environment, and the like may be imparted to the microcapsules, and the microcapsules are currently applied as a functional material to various fields including foods, pharmaceuticals and the like.

As a method for forming the microcapsules, such a method has been known that a core material for forming the core of the capsules and a shell material for forming the shell (both of which materials are in liquid form) are used, and the core material is covered with the shell material, thereby forming the capsules. For example, the following method is proposed (see, for example, JP-A-2005-224647). The shell material having a smaller specific gravity than the core material is floated on the liquid surface of the core material, and the shell material is retained in the form of a liquid film. Bubbles are formed and broken in the vicinity of the interface between the core material and the shell material (immediately beneath the liquid surface of the core material), and by means of pressure formed through the breakage of the bubbles, the core material is discharged toward the liquid film of the shell material with the pressure formed, and the core material is covered and wrapped with the shell material, thereby forming the microcapsules.

The method disclosed in JP-A-2005-224647 facilitates the formation of microcapsules having a shell with a uniform thickness.

Since the method disclosed in JP-A-2005-224647 forms capsules by generating pressure formed through the breakage of the bubbles, however, it is difficult to control precisely the particle diameter of the capsules formed, and thus the method is not suitable for forming capsules with high accuracy. Furthermore, the yield rate of the core material upon forming the capsules may be lowered since the core material is necessarily retained in the form of a liquid film.

JP-A-2005-224647 does not disclose a method of curing the shell after wrapping the core material with the shell material. Accordingly, only capsules having a core material wrapped by a liquid (shell material) may be formed, but capsules having a shell that is cured to suitable hardness may not be formed. The capsules with a liquid shell fail to exhibit sufficiently such functions as protecting the core from the external environment, and thus are limited in application.

SUMMARY

An advantage of some aspects of the invention is to provide an encapsulation device that is capable of curing a shell to suitable hardness and forming capsules with accuracy.

An aspect of the invention is directed to an encapsulation device that includes: a fluid injection device that injects a first liquid forming a core; a liquid film holder that holds in film form a second liquid forming a shell containing the core; and a liquid contact device that makes the shell in contact with a third liquid, the first liquid being injected toward a liquid film of the second liquid retained by the liquid film holder to form a core, the core being wrapped with the second liquid on passing through the liquid film of the second liquid, thereby forming the shell, and the shell being made in contact with the third liquid to induce chemical reaction.

Other aspects and advantages of the invention will be apparent from the following description.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
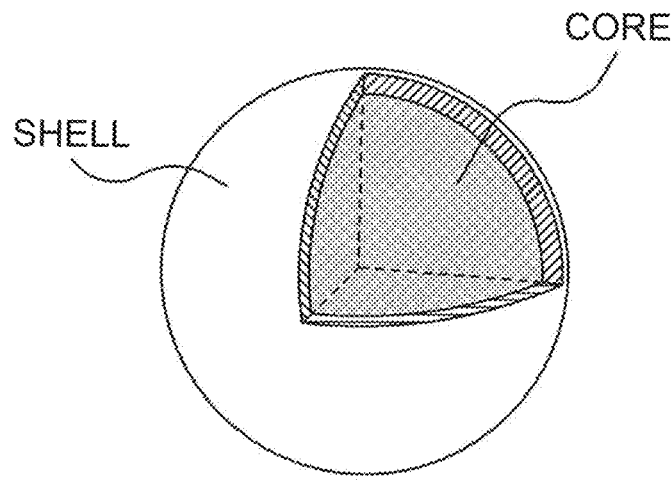
FIG. 1A is a conceptual illustration showing a capsule.

At least the following will be apparent from the description herein and the accompanying drawings.

An encapsulation device includes: a fluid injection device that injects a first liquid forming a core; a liquid film holder that holds in film form a second liquid forming a shell containing the core; and a liquid contact device that makes the shell in contact with a third liquid, in which the first liquid is injected toward a liquid film of the second liquid retained by the liquid film holder to form a core, the core is wrapped with the second liquid on passing through the liquid film of the second liquid, thereby forming the shell, and the shell is made in contact with the third liquid to induce chemical reaction.

According to the encapsulation device, the shell of the capsules can be cured to suitable hardness, thereby forming the capsules with accuracy.

In the encapsulation device, it is preferred that the liquid contact device has a liquid reservoir that reserves the third liquid in liquid form, and the second liquid is made in contact with the third liquid by making the core wrapped with the second liquid to enter the liquid reservoir.

According to the encapsulation device, the capsules can be formed while the thickness and the hardness of the shell are controlled appropriately depending on the purpose and the demanded functions of the capsules.

In the encapsulation device, it is preferred that the liquid contact device has a mist generator that mists the third liquid in mist form, and the second liquid is made in contact with the third liquid by misting the third liquid from the mist generator to an area, toward which the core wrapped with the second liquid is moved.

According to the encapsulation device, the shell can be cured uniformly, and the capsules thus completed can be easily recovered.

In the encapsulation device, it is preferred that the second liquid is an aqueous solution containing a polysaccharide or a protein, the third liquid is an aqueous solution containing a polyvalent metal salt, and the second liquid is made in contact with the third liquid to induce crosslinking reaction, thereby curing the shell.

According to the encapsulation device, capsules that are harmless to human bodies and have high applicability to medical fields and the like can be formed.

In the encapsulation device, it is preferred that a distance from the fluid injection device to a surface of the liquid film of the liquid film holder is from 10 to 10,000 μm.

According to the encapsulation device, the injection velocity of the core can be prevented from being decreased, and the core can be prevented from being evaporated.

In the encapsulation device, it is preferred that a distance from the surface of the liquid film of the liquid film holder to a liquid surface of the liquid contact device is from 0.1 to 50 mm.

According to the encapsulation device, the shell can be prevented from being evaporated.

In the encapsulation device, it is preferred that the fluid injection device has a nozzle that injects droplets of the first liquid, and a device that is driven by an electric voltage signal to make the droplets inject from the nozzle, and a size of the droplets injected from the fluid injection device is controlled by changing a voltage of the electric voltage signal.

According to the encapsulation device, capsules having a target size can be formed with high accuracy.

In the encapsulation device, it is preferred that the fluid injection device has a plurality of the nozzles, and the droplets are injected from the plurality of the nozzles.

According to the encapsulation device, plural capsules can be formed with high efficiency.

A medical capsule is produced by the encapsulation device described above.

An encapsulation method includes: forming a core by injecting a first liquid toward a liquid film of a second liquid retained in film form; wrapping the core with the second liquid by passing the core through the liquid film of the second liquid, thereby forming a shell containing the core; and making the shell in contact with a third liquid to induce chemical reaction.

An encapsulation device includes: a fluid injection device that injects droplets of a first liquid; a second liquid holder that holds in film form a second liquid; and a third liquid holder that holds in film form a third liquid, the droplets injected from the fluid injection device are passed through a liquid film of the second liquid held by the second liquid holder, thereby wrapping the droplets with the second liquid, and the droplets wrapped with the second liquid are passed through a liquid film of the third liquid held by the third liquid holder, thereby wrapping the droplets wrapped with the second liquid with the third liquid.

According to the encapsulation device, capsules can be formed by passing the core through plural liquid films.

In the encapsulation device, it is preferred that the encapsulation device further includes a liquid contact device that makes the shell formed by wrapping the liquid droplets wrapped with the second liquid with the third liquid, in contact with a fourth liquid, and the shell is made in contact with the fourth liquid to induce chemical reaction.

According to the encapsulation device, multilayer capsules having a shell in a cured state can be formed.

In the encapsulation device, it is preferred that the third liquid is an aqueous solution containing a polysaccharide or a protein, the fourth liquid is an aqueous solution containing a polyvalent metal salt, and the third liquid is made in contact with the fourth liquid to induce crosslinking reaction.

According to the encapsulation device, capsules that are harmless to human bodies and have high applicability to medical fields and the like can be formed.

In the encapsulation device, it is preferred that a core is formed with the droplets of the first liquid, a first shell is formed with the second liquid wrapping the core, and the first shell is made in contact with the third liquid to induce chemical reaction, thereby curing the first shell.

According to the encapsulation device, the shell of the capsules can be appropriately cured.

In the encapsulation device, it is preferred that the encapsulation device further includes a fourth liquid holder that holds in film form a fourth liquid, and a fifth liquid holder that holds in film form a fifth liquid, the core having the first shell cured with the third liquid is passed through a liquid film of the fourth liquid held by the fourth liquid holder, thereby wrapping the core with the fourth liquid to form a second shell, and the core having the second shell is passed through a liquid film of the fifth liquid held by the fifth liquid holder and come into contact with the fifth liquid to induce chemical reaction, thereby curing the second shell.

According to the encapsulation device, capsules having plural shells, each of which are cured, can be formed.

In the encapsulation device, it is preferred that the second liquid is an aqueous solution containing a polysaccharide or a protein, the third liquid is an aqueous solution containing a polyvalent metal salt, and the second liquid is made in contact with the third liquid to induce crosslinking reaction.

According to the encapsulation device, capsules that are harmless to human bodies and have high applicability to medical fields and the like can be formed.

A medical capsule is produced by the encapsulation device described above.

An encapsulation method includes: injecting droplets of a first liquid; passing the injected droplets through a liquid film of a second liquid held in film form, thereby wrapping the droplets with the second liquid; and passing the droplets wrapped with the second liquid through a liquid film of a third liquid held in film form, thereby wrapping the droplets wrapped with the second liquid with the third liquid.

Outline

Capsules

FIG. 1A is a conceptual illustration showing a capsule formed in one embodiment of the invention. The capsule is constituted by a core and a shell containing the core. Examples of a core material forming the core include a material having an active ingredient dissolved therein, a material having an active ingredient dispersed therein, and an active ingredient that is present in the form of a solid or a gas. The capsules have been used in various fields of art including foods, medicated cosmetics and medical drugs, and the capsules have wide varieties of the sizes (capacities of the content) and the thickness of the shell depending on the purposes thereof.

In the description herein, a capsule that has one or more shell per one core may be referred to as a multilayer capsule.

Figure 1B:
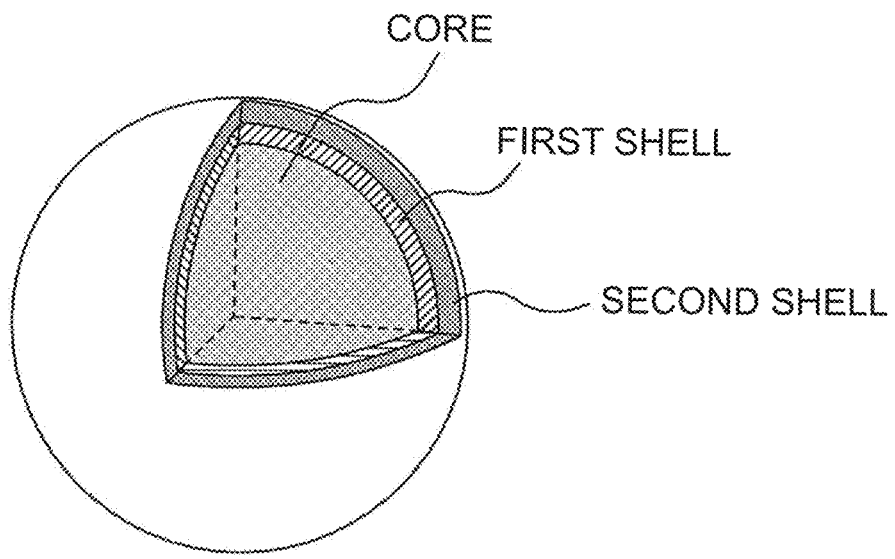
FIG. 1B is a conceptual illustration showing a capsule having plural shells.
Figure 2:
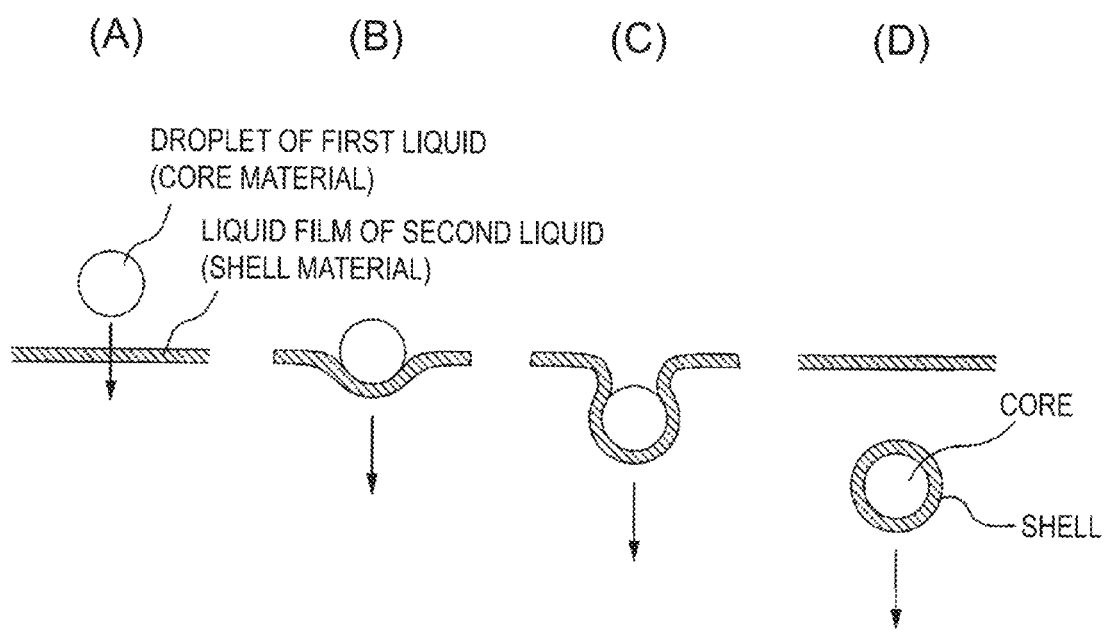
FIGS. 2A to 2D are schematic illustrations showing a process of forming a shell.

A multilayer capsule that has plural shells per one core may also be formed. FIG. 1B is a conceptual illustration showing a multilayer capsule having plural shells. The multilayer capsule shown in FIG. 1B has a core, a first shell containing the core, and a second shell containing the first shell, and therefore the capsule is a multilayer capsule having a two-layer shell. A capsule having various functions may be formed by imparting different functions to the core and the first shell, respectively. For example, the core and the first shell may be drugs having functions different from each other, and both of them may be protected by the second shell. A multilayer capsule having three or more shells may be formed.

Formation Method of Capsule

An embodiment of a method of forming a capsule having a core and a shell will be described briefly. In this embodiment, a capsule is formed with plural kinds of liquids as raw materials. A first liquid is used as a core material for forming the core, and a second liquid is used as a shell material for forming the shell. Liquid materials may be optimally selected for the first liquid and the second liquid depending on the functions and purposes of the capsules to be formed.

Upon forming the capsule, the core material (the first liquid) is passed through the shell material formed in the form of a thin film (a liquid film of the second liquid). Upon passing the core material through the liquid film of the second liquid, the shell material wraps the entire core material, thereby forming a shell.

FIGS. 2A to 2D are schematic illustrations showing a process of forming a shell. The states (A) to (D) show in time series the process where a droplet of a core material is passed through a liquid film of a shell material. In FIGS. 2A to 2D, the core material is passed substantially vertically from above through the liquid film held horizontally.

(A) The core formed of a liquid droplet of the first liquid (the core material) enters into the liquid film formed of the second liquid (the shell material) at a prescribed velocity (e.g., a velocity by which the core can be passed through the liquid film). (B) The core in contact with the liquid film of the second liquid continues to proceed and goes to penetrate the liquid film, and thereby the liquid film is deformed to wrap around the core. The first liquid and the second liquid are different from each other in properties including composition, specific gravity, viscosity, surface tension and the like (for example, a combination of liquids that form a strong interface, such as a combination of an aqueous liquid and an oily liquid), and the liquids are not mixed immediately after the contact. (C) The core wrapped with the liquid film continues to proceed, and at the time when the core is passed through the initial position of the liquid film, the most portion of the core is wrapped with the second liquid (the shell material). The liquid film is in a state where a hole is formed after passing the core, and the second liquid goes to migrate toward the hole to recover the initial state without the hole. (D) When the core is completely passed through the liquid film, the entire of the core is wrapped with the second liquid (the shell material), thereby forming a shell containing the core. The hole formed in the liquid film after passing the core is closed with the second liquid.

A capsule having a core wrapped with a shell is formed through the aforementioned process. For forming a capsule having two or more shells, plural liquid films of shell materials are provided, and the operations shown by (B) to (D) are repeated.

In the state (D), the shell is in the form of a liquid (the second liquid). In this embodiment, the shell thus formed is made in contact with a third liquid as a shell curing agent to induce chemical reaction. The shell is imparted with suitable hardness through the chemical reaction, thereby forming a capsule that is resistant to the external environment.

The term "capsule" referred herein means a state where at least one of a core and a shell (or plural shells) is cured. For example, a two-layer capsule means a state where at least one of the droplets of the core material and the first shell is cured.

A state where none of a core and a shell (or plural shells) are cured is referred to as a multiphase droplet. For example, a two-phase droplet means a state where none of the droplets of the core material and the first shell are cured.

The term "cure" means increase of hardness, and includes increase of viscosity of a liquid, a property changes from liquid to solid, and the like, but is not limited to a strength change inherent to solid materials.

First Embodiment

An encapsulation device 1 using a fluid injection device according to a first embodiment of the invention will be described.

In the encapsulation device 1, a minute amount of a liquid is injected by an ink-jet method, thereby forming capsules having a minute size, i.e., capsules having a nanometer (nm) order or micrometer (µm) order diameter. For example, so-called microcapsules (microspheres) having a capacity of approximately from 0.1 to 500 pL (picoliter) may be formed.

Structure of Encapsulation Device 1

Figure 3:
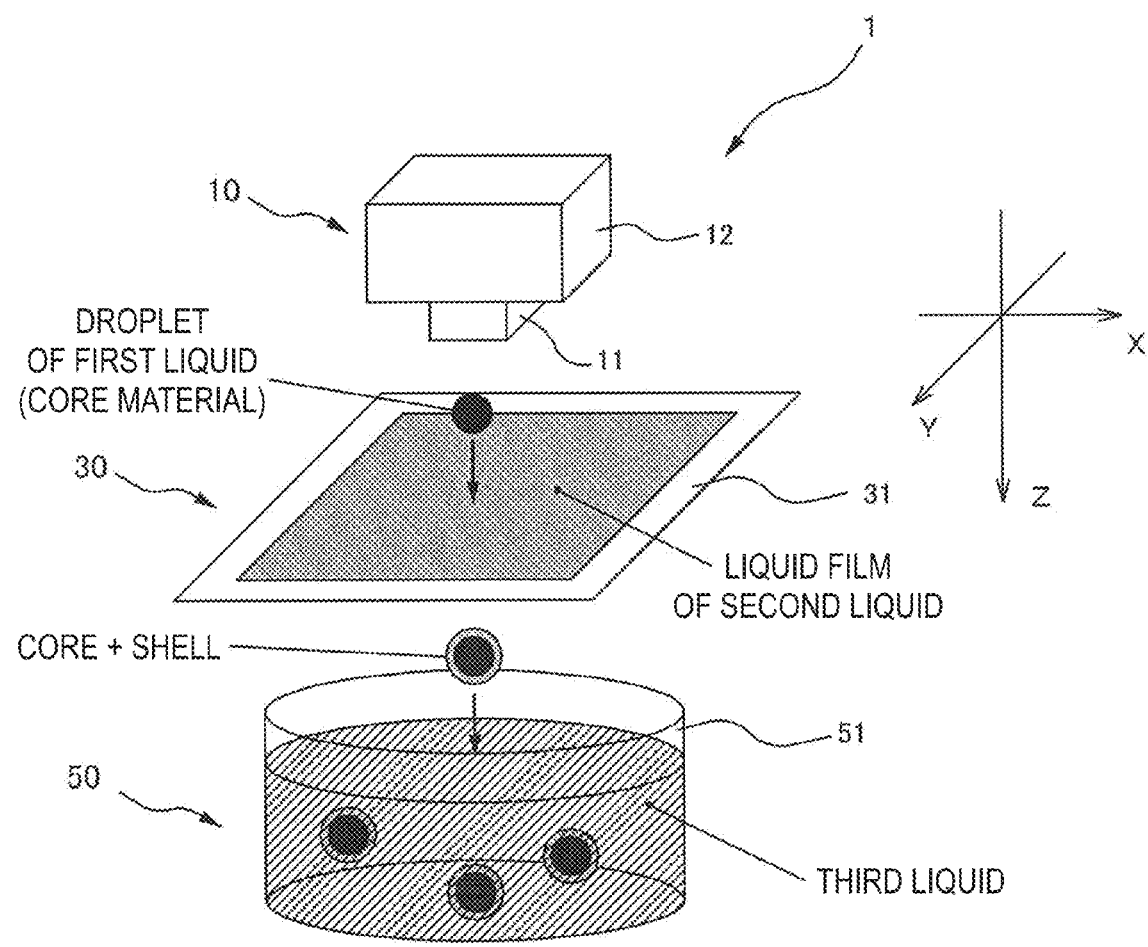
FIG. 3 is a schematic diagram showing a structure of one embodiment of an encapsulation device.

FIG. 3 is a schematic diagram showing a structure of the encapsulation device 1. The encapsulation device 1 has a fluid injection device 10, a second liquid holder 30 and a liquid contact device 50.

As shown in FIG. 3, a coordination system with X axis, Y axis and Z axis is set. The Z axis is a vertical direction (the downward direction in FIG. 3), the X axis is a direction perpendicular to the Z axis, and the Y axis is a direction perpendicular to both the Z axis and the X axis. In FIG. 3, the fluid injection device 10, the second liquid holder 30 and the liquid contact device 50 are aligned in the Z axis direction, but the positional relationship thereof may be modified.

The fluid injection device 10 injects the first liquid (the core material) to form a core of a microcapsule. The liquid injection device 10 has an injection head 11, a first liquid tank 12 and a head controller HC (which is not shown in the figure).

The injection head 11 injects the first liquid as droplets. The first liquid tank 12 stores the first liquid and feeds the first liquid to the injection head 11. The head controller HC generates a driving signal, which is a voltage waveform signal, for driving the injection head 11.

Figure 4:
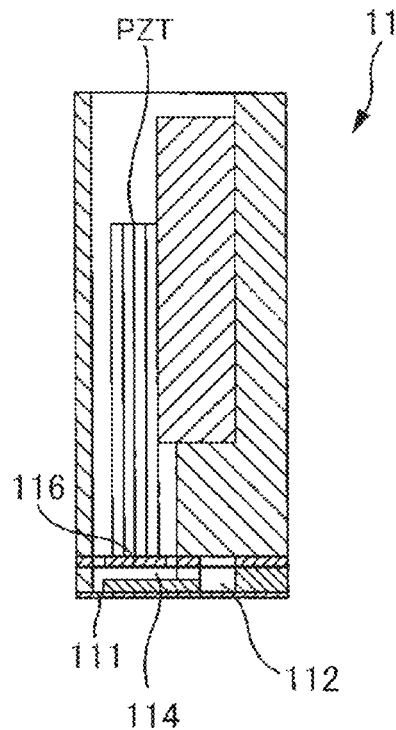
FIG. 4 is a schematic cross sectional view showing a structure of an injection head.

FIG. 4 is a schematic cross sectional view showing the structure of the injection head 11. The injection head 11 has a nozzle 111, a piezoelectric device PZT, a liquid feeding path 112, a nozzle communication path 114 and an elastic plate 116.

The first liquid stored in the first liquid tank 112 is fed to the nozzle communication path 114 through the liquid feeding path 112. The piezoelectric device PZT is applied with a voltage waveform signal containing plural pulses as a driving signal generated in the head controller HC. The piezoelectric device PZT is expanded and contracted by the driving signal and vibrates the elastic plate 116, with which the capacity of the nozzle communication path 114 is changes, and thereby the first liquid fed to the nozzle communication path 114 is injected from the nozzle 111 according to the amplitude of the driving signal.

The first liquid thus injected becomes spherical droplets due to the surface tension thereof. Accordingly, the size of the droplets (i.e., the amount of the liquid injected) can be controlled by changing the amplitude (the magnitude of voltage) of the driving signal applied to the piezoelectric device PZT, thereby forming a core of capsules having a target size accurately.

When the first liquid contains oxygen molecules dissolved therein, bubbles may be formed in the nozzle communication path 114, and therefore, the first liquid is preferably deaerated in advance.

The nozzle 111 has a diameter, for example, of 20 μm, and may inject the first liquid at an injection frequency of 10 Hz or more. The injection frequency may be controlled by changing the frequency of the driving signal, thereby changing the formation efficiency of the core of capsules.

The second liquid holder 30 has a liquid film holding frame 31.

The liquid film holding frame 31 holds the second liquid (the shell material) in the form of a thin film. The second liquid is surrounded by the liquid film holding flame 31 and thereby forms a liquid film with the liquid film holding frame 31 as an outer edge. The material of the liquid film holding frame 31 may be any one that is capable of holding the liquid film, and examples of the material in the first embodiment include a metal (such as stainless steel, aluminum, copper, gold, silver, brass, titanium, carbon steel and white metal) and a resin (such as an acrylic resin, polyurethane, a silicone resin, an epoxy resin, a melamine resin, a phenol resin, polyethylene, polypropylene, polystyrene, polyvinyl chloride and nylon). The shape of the liquid film holding frame 31 may be arbitrarily determined, as far as it can hold the liquid film. The thickness of the liquid film holding frame 31 may be determined in consideration of the thickness of the liquid film to be held.

The liquid contact device 50 stores a third liquid (a shell curing agent) in liquid form. In the liquid contact device 50, the third liquid is made in contact with the second liquid to induce chemical reaction.

The liquid contact device 50 has a liquid reservoir tank 51. The liquid reservoir tank 51 is a container capable of storing a liquid, and forms a liquid phase of the third liquid shown by the hatched portion in FIG. 3. A material to be in contact enters into the liquid phase through the upper opening of the liquid reservoir tank 51 and is made in contact with the third liquid. In the first embodiment, the droplets of the first liquid wrapped with the second liquid (i.e., the two-phase droplets) enter the third liquid, and the second liquid is made in contact with the third liquid to induce chemical reaction, thereby curing the second liquid to suitable hardness.

The liquid reservoir tank 51 has a recovery mechanism (which is not shown in the figure) that recovers the capsules having been made in contact with the third liquid. Examples of the recovery mechanism include a filtering device that filters the capsules thus formed from the third liquid. Accordingly, the liquid contact device 50 also has a function of a capsule recovery device.

Capsule Formation Process

Figure 5:
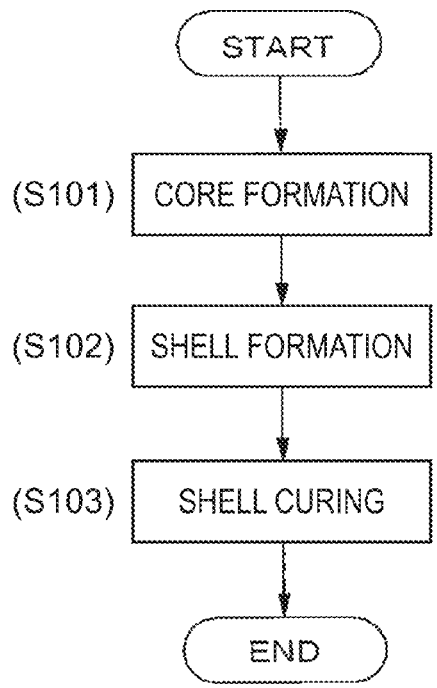
FIG. 5 is a flow chart showing a capsule formation process according to a first embodiment.

FIG. 5 is a flow chart showing the capsule formation process according to the first embodiment. In the first embodiment, capsules are formed through core formation (S101), shell formation (S102) and shell curing (S103).

S101: Core Formation

A core of the capsule is formed with a droplet of the core material (the first liquid) injected from the fluid injection device 10. Examples of the core material used include an aqueous solution containing an active ingredient (such as hydroquinone, ceramide, bovine serum albumin, y-globulin, lipiodol, bifidobacteria, vitamins, hyaluronic acid and IPS cells).

As shown in FIG. 3, the droplets of the core material (the first liquid) are injected toward the liquid film of the shell material (the second liquid) held by the second liquid holder 30. The core material may not be necessarily injected in the direction perpendicular to the liquid film of the shell material, and may be injected in an oblique direction.

The injection amount of the core material may be determined depending on the size of the core (capacity) of the capsule to be formed since the droplet of the first liquid becomes directly the core. In other words, the size of the capsule can be freely determined by controlling the injection amount of the core material.

This means that the yield rate of the core material is considerably high. The core material thus injected forms the core with high efficiency, and there is substantially no waste of the core material, thereby suppressing the raw material cost of the capsule. This is effective in the case where an expensive substance is used as the core material (for example, a medical material is used as the core material for forming medical capsules). The amount of the liquid to be wasted is small, which is effective also in view of environmental protection. The amount of the liquid may be optimized not only in medical capsules, but also in capsules for cosmetics, capsules for foods, and the like.

The injection velocity of the core material may be set such a value that is capable of penetrating the liquid film in the shell formation (S102). That is, the velocity may be set in such a manner that the injected droplets of the core material have a kinetic momentum sufficient for penetrating through the liquid film. The velocity to be set may vary depending on the conditions including the thickness of the liquid film, the viscosity and the surface tension of the material of the liquid film, the injection amount and the density of the core material, and the like. The velocity may also vary depending on the positional relation ship (the distance) of the fluid injection device 10 and the second liquid holder 30.

The minimum injection velocity capable of passing the core material through the liquid film may be investigated in advance by performing experiments under the conditions where the capsules are actually formed, and the minimum injection velocity may be used as a threshold value. For example, the threshold values may be determined for each of the sizes of the core to be formed and the liquid materials used. The head controller HC drives the piezoelectric device PZT by referring to the threshold values thus set, and the core material is injected at a velocity larger than the prescribed value.

S102: Shell Formation

The core thus formed enters the liquid film of the shell material (the second liquid) held by the second liquid holder 30. Upon passing through the liquid film, the core is wrapped with the shell material to form a shell, thereby forming a two-phase droplet (see FIGS. 2A to 2D).

Examples of the shell material (the second liquid) used include an aqueous solution containing a polysaccharide or a protein (such as sodium alginate, calcium alginate, potassium alginate, ammonium alginate, ethylcellulose, methylcellulose, pectin, Gellan gum, chitosan, collagen and fibrinogen). Alginate salts are substantially harmless to human bodies, and the use thereof as the shell material enhances the application range of the capsule.

Liquids that are less miscible with each other may be selected so that the shell material (the second liquid) and the core material (the first liquid) can maintain the separated state of the materials for a certain period of time.

The second liquid holder 30 is disposed horizontally, and the position thereof is controlled in such a manner that the core material (the first liquid) injected from the fluid injection device 10 arrives at the liquid film from above. When the core enters the liquid film perpendicularly, a uniform shell having less unevenness in thickness may be formed. However, the shell may be formed with the second liquid holder 30 that is oblique from the horizontal plane being placed, as far as the liquid film is maintained.

The distance between the position where the liquid film of the shell material is held and the fluid injection device 10 is preferably as small as possible. When the core material migrates a long distance in the air after the injection, the core material may be evaporated during the migration, and the size of the core may be diminished. In the case where capsules having a minute size is formed, in particular, the core material is liable to be evaporated, and it is necessary to keep attention on this point.

In the case where the diameter of the microcapsule is less than 100 μm, in order that the velocity of passing the liquid film may not decrease the distance between the liquid film and the fluid injection device 10 is advantageously as small as possible. In the first embodiment, the second liquid holder 30 may be disposed in such a manner that the distance from the injection of the core material to the arrival thereof to the liquid film of the shell material is approximately from 10 to 10,000 μm. The distance is more preferably from 10 to 5,000 μm since it is advantageous in evaporation of the droplet in view of velocity decrease.

In the case where the diameter of the microcapsule is from 100 to 1,000 μm, the second liquid holder 30 may be disposed in such a manner that the distance from the injection of the core material to the arrival thereof to the liquid film of the shell material is approximately from 1 to 1,000 mm. The distance is more preferably from 1 to 300 mm since it is advantageous in evaporation of the droplet in view of velocity decrease.

The environment where the droplets migrate is preferably windless for preventing deterioration of the accuracy in arrival of the droplets and also is preferably high humidity for preventing evaporation of the core material.

The shell is formed with the second liquid (the shell material) as a raw material, and therefore the second liquid may be consumed through repetition of the capsule formation process, which decreases the thickness of the liquid film. In this case, the thickness of the shell may not be maintained constant, and the liquid film tends to be broken. The repetition of the capsule formation process may cause contamination of the liquid film with impurities (such as bubbles, a residual matter of the core material, and satellites).

Accordingly, the liquid film may be rebuilt at a prescribed timing during the capsule formation process, or the liquid film is replaced along with the liquid film holding frame 31, thereby preventing the conditions of the liquid film from being fluctuated. Consequently, the shell thus formed may have high quality maintained. The timing where the liquid film is rebuilt or replaced may be determined in consideration of the duration of operation time of the capsule formation process and the total amount of the core material that has been injected from the fluid injection device 10.

S103: Shell Curing

After forming the shell, the shell of the two-phase droplet is cured in the liquid contact device 50. The two-phase droplet having been passed through the liquid film of the shell material enters directly the liquid reservoir tank 51. The shell curing agent (the third liquid) is made in contact with the shell (the second liquid) to induce chemical reaction, thereby forming a capsule having a cured shell (i.e., a two-layer capsule).

Examples of the shell curing agent (the third liquid) used include an aqueous solution containing a polyvalent metal salt having a gelation inducing factor (for example, an aqueous solution containing a calcium salt, such as calcium chloride, calcium acetate, calcium nitrate, calcium citrate, calcium lactate and calcium carbonate, an aqueous solution containing an aluminum salt, such as aluminum chloride, aluminum nitrate, aluminum sulfate, aluminum acetate and aluminum phosphate, an aqueous solution containing a manganese salt, such as manganese chloride, manganese nitrate, manganese acetate and manganese sulfate, an aqueous solution containing a magnesium salt, such as magnesium chloride, magnesium nitrate, magnesium acetate and magnesium sulfate, and an aqueous solution containing an iron salt, such as ferrous phosphate and ferric phosphate).

The distance between the second liquid holder 30 and the liquid reservoir tank 51 relates to evaporation of the droplets and the velocity of the droplets entering the third liquid. In the case where capsules having a diameter of less than 100 μm are formed, the distance therebetween is preferably from 0.1 to 100 mm, and particularly preferably from 0.1 to 50 mm. In the case where capsules having a diameter of from 100 to 1,000 μm are formed, the distance therebetween is preferably from 0.1 to 15 cm, and particularly preferably from 0.1 to 10 cm. When the distance between the second liquid holder 30 and the liquid reservoir tank 51 is too large, the shell material tends to be evaporated during migration. The environment where the droplets fly is preferably windless and high humidity.

In the shell curing (S103), the shell material (the second liquid) is made in contact with the shell curing agent (the third liquid) and is gelled through chemical reaction, such as crosslinking reaction, polymerization reaction and polymer reaction. The term "gelation" herein includes a change where the viscosity is increased, and may be referred to as "curing".

Chemical Reaction

Figure 6:
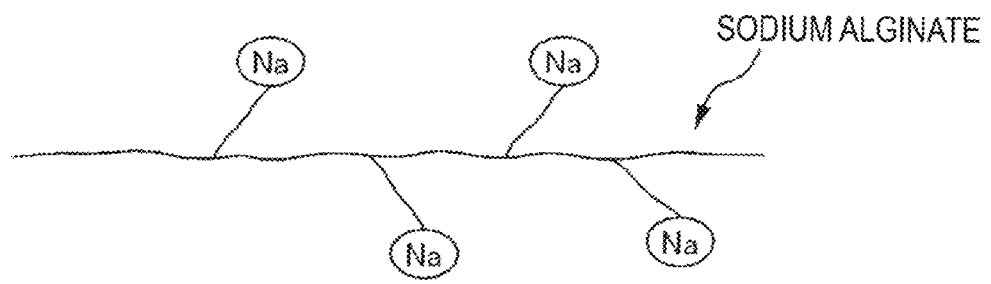
FIG. 6 is a schematic illustration showing sodium alginate.
Figure 7:
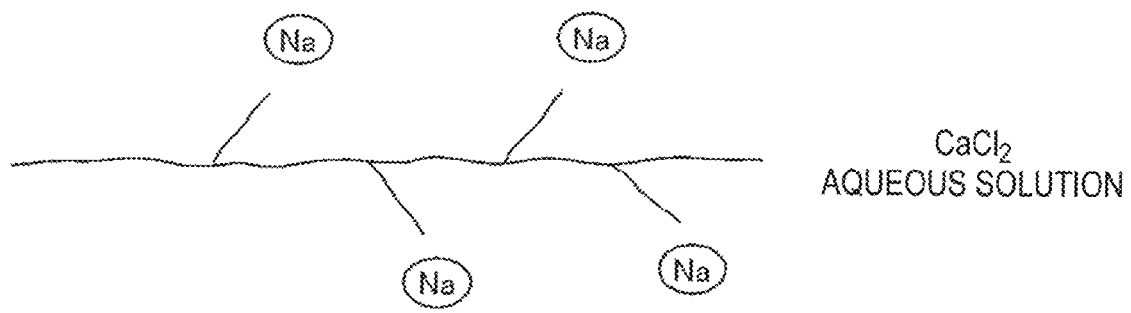
FIG. 7 is a schematic illustration showing an intermediate state where sodium alginate is converted to calcium alginate.
Figure 8:
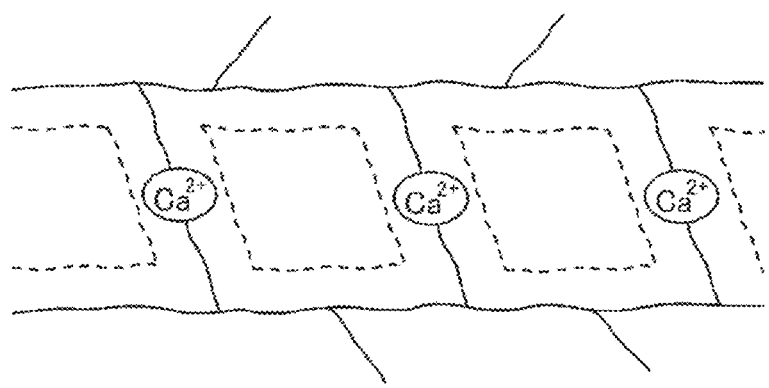
FIG. 8 is a schematic illustration showing calcium alginate gel.

The chemical reaction where an sodium alginate aqueous solution is used as the shell material (the second liquid) and a calcium chloride aqueous solution is used as the shell curing agent (the third liquid) will be described. FIG. 6 is a schematic illustration showing sodium alginate. FIG. 7 is a schematic illustration showing an intermediate state where sodium alginate is converted to calcium alginate. FIG. 8 is a schematic illustration showing calcium alginate gel.

In sodium alginate ($C_6H_7O_6Na$), a monovalent sodium ion is bonded to alginic acid (FIG. 6). Upon making sodium alginate in contact with calcium chloride ($CaCl_2$) aqueous solution, a divalent calcium ion ($Ca^{2+}$) is replaced by a sodium ion ($Na^+$) of sodium alginate (FIG. 7). At this time, a sodium ion ($Na^+$) is a monovalent ion, whereas a calcium ion ($Ca^{2+}$) is a divalent ion, and therefore, two sodium ions ($Na^+$) are replaced by one calcium ion ($Ca^{2+}$). Two sodium ions ($Na^+$) are released off from two molecules of sodium alginate and replaced by one calcium ion ($Ca^{2+}$) (FIG. 8), and thereby crosslinking aggregation occurs between two molecules of alginic acid, which are thus gelled. This type of chemical reaction may be referred to as crosslinking reaction.

In calcium alginate gel, water molecules migrate between the interior and exterior of the gel through the areas surrounded with the broken lines in FIG. 8. The presence of water molecules in the areas surrounded with the broken lines impart elasticity to the gel. Furthermore, in the case of ingesting to a human body the formation of the hydrophilic shell facilitates formation of capsules that have high biocompatibility, and also facilitates control of the osmotic pressure between the core and the external environment through the shell.

In the first embodiment, the hardness of the shell may be controlled by utilizing the property of the chemical reaction (crosslinking reaction). For example, the hardness of the shell may be controlled by changing the contact time of the shell material (the second liquid) and the shell curing agent (the third liquid). In the case where capsules are recovered immediately after the two-phase droplets having the shell enter the shell curing agent stored in the liquid reservoir tank 51, the contact time of the shell material and the shell curing agent is short, and the chemical reaction proceeds in the surface of the shell but does not proceed sufficiently in the interior of the shell. Accordingly, soft capsules having a thin shell may be formed. In the case where capsules are recovered after a sufficient period of time from the enter of the two-phase droplets into the liquid reservoir tank 51 elapse, the chemical reaction proceeds sufficiently in the interior of the shell, thereby forming hard capsules having a thick shell. The rate of the chemical reaction is influenced by the concentrations of the liquids. Accordingly, the curing rate of the shell may be controlled by changing the concentrations of the shell material (the second liquid) and the shell curing agent (the third liquid), and thereby the hardness of the shell may be controlled within a desired period of time.

Capsules capable of being adapted to various applications may be formed by controlling arbitrarily the thickness and the hardness of the shell. For example, in the case where the capsules are applied to a medical field, the period of time from the ingestion of the capsules by human bodies to the exposure of the internal substance (i.e., the core) through breakage of the shell may be controlled by changing the hardness of the shell. Specifically, capsules constituted by a core formed with a medical drug and a shell wrapping the core are formed, and the capsules may be applied to DDS (drug delivery system), for example, the drug (core) reaches an affected area without absorption and decomposition after the ingestion by human bodies, and at the time when the drug reaches the affected area, the drug is released.

The capsules having a cured shell are recovered by the recovery mechanism of the liquid contact device 50.

By the encapsulation device according to the first embodiment, capsules having a target size can be formed with high accuracy. The formation efficiency of the capsules may be controlled by changing the frequency of the driving signal for changing the injection timing of the first liquid (the core material). A high yield rate of the core material may be obtained, which is advantageous in cost.

The capsules may be formed while controlling the thickness and the hardness of the shell suitably depending on the purposes of the capsules and the functions demanded thereby by changing the contact time of the second liquid (the shell material) and the third liquid (the shell curing agent).

Various kinds of liquids may be combined as raw materials of capsules. For example, various kinds of liquids may be used as the second liquid (the shell material), as far as the liquid can be held as a liquid film by the second liquid holder 30 and can be cured in the liquid contact device 50. Consequently, the materials may be selected from a wide variety of materials, and thereby a wide variety of capsules may be formed.

Modified Embodiment

The encapsulation device 1 may have plural injection heads 11 disposed in the fluid injection device 10.

Figure 9:
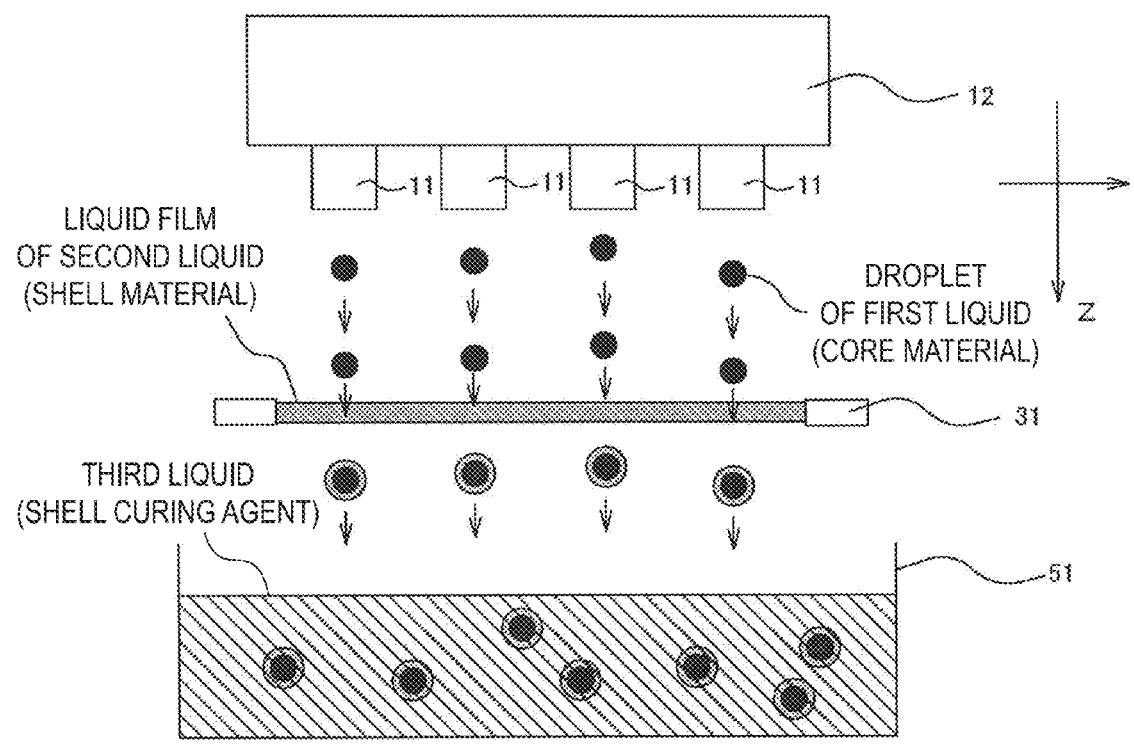
FIG. 9 is a schematic diagram showing a structure of a modified embodiment of an encapsulation device.

FIG. 9 is a schematic diagram showing a modified embodiment of an encapsulation device 1. In the modified embodiment, four injection heads 11 are provided in the fluid injection device 10, and four droplets (cores) may be injected simultaneously. The amount of the droplets injected from the fluid injection device 10 is increased, and thus plural capsules are formed simultaneously, thereby enhancing the formation efficiency of the capsules.

Furthermore, plural nozzles 111 may be provided in the injection head 11, thereby forming the capsules with higher efficiency. In this case, the piezoelectric device PZT is provided for each of the nozzles.

Second Embodiment

Figure 10:
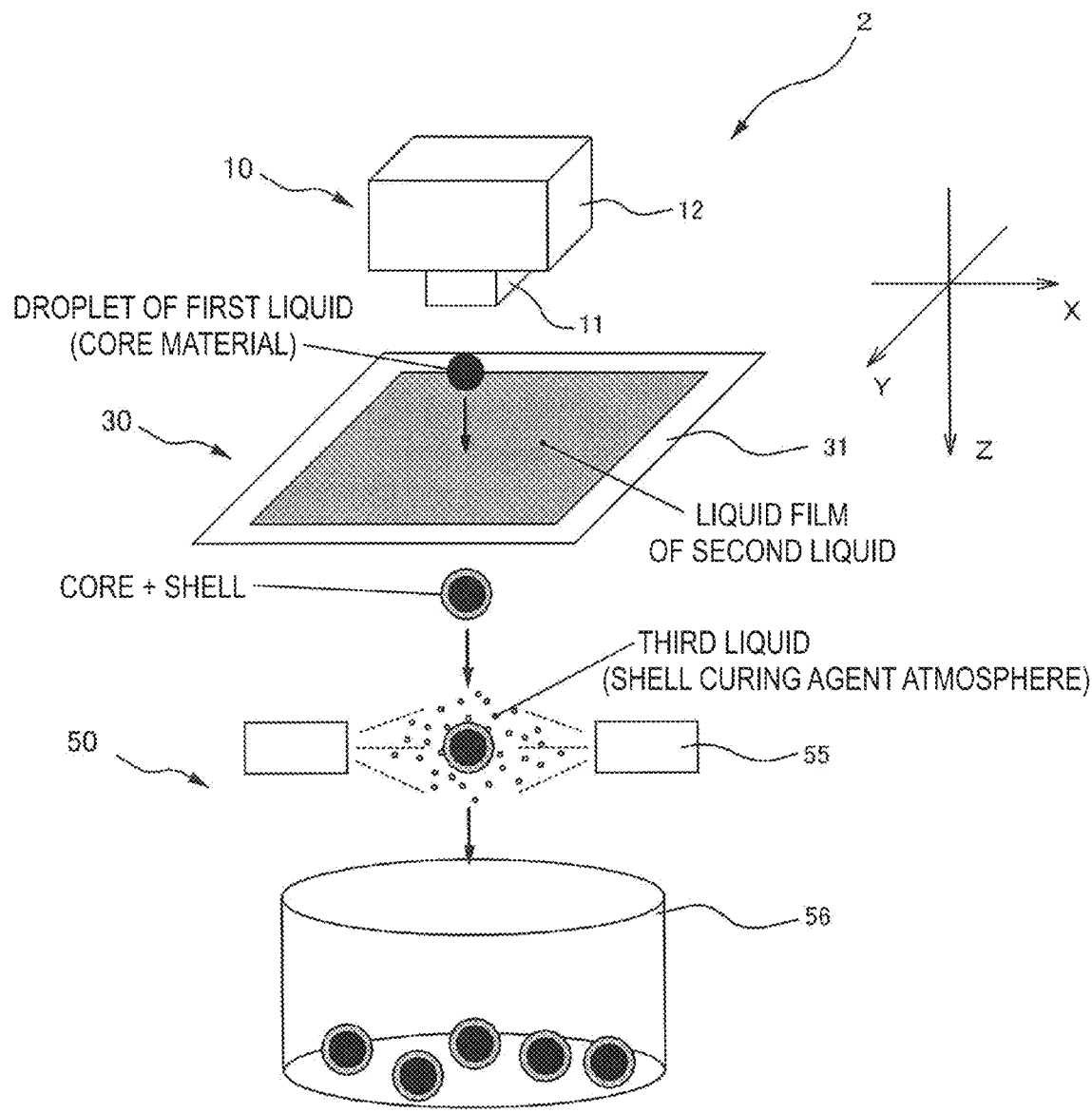
FIG. 10 is a schematic diagram showing a structure of one embodiment of an encapsulation device according to a second embodiment.

An encapsulation device according to a second embodiment of the invention has a liquid contact device 50 that has a different structure from that of the first embodiment. FIG. 10 is a schematic diagram showing the structure of one embodiment of an encapsulation device 2 according to the second embodiment. In the encapsulation device 2, a fluid injection device 10 and a second liquid holder 30 are substantially the same as in the encapsulation device 1.

The liquid contact device 50 of the encapsulation device 2 according to the second embodiment has a mist generator 55 and a capsule recovery device 56.

The mist generator 55 mists the third liquid (the shell curing agent) in the form of mist, and distributes the third liquid to a prescribed area in the air, as shown in FIG. 10. In other words, an atmosphere is formed with fine particles of the shell curing agent (which may be referred to as a shell curing agent atmosphere) in a prescribed area in the air. The mist generator 55 has, for example, a spray nozzle.

The capsule recovery device 56 may be a vessel for recovering completed capsules, and may be disposed at the most downstream side in the migration direction of the capsules.

Capsule Formation Process

The capsule formation process in the second embodiment is substantially the same as that in the first embodiment (FIG. 5), but the shell curing is different from the first embodiment. In the second embodiment, the shell is imparted with suitable hardness in a gas phase.

The two-phase droplet having been passed through the liquid film of the second liquid is made in contact with the fine particles the shell curing agent (the third liquid) upon passing through the shell curing agent atmosphere, which is disposed in the course of the migration direction of the droplets. Chemical reaction is induced at a portion on the surface of the two-phase droplet where the shell material is made in contact with the shell curing agent, and the hardness of the portion is changed. For example, in the case where an aqueous solution containing an alginate salt is used as the shell material and an aqueous solution containing calcium chloride is used as the shell curing agent, crosslinking reaction is induced in the contact portion, and thereby the shell is cured. The fine particles of the shell curing agent are distributed uniformly in the gas phase, and thus the shell curing agent is made uniformly in contact with the shell material. Consequently, the chemical reaction proceeds uniformly, which facilitates uniform hardness over the surface of the shell.

Capsules having a shell that is suitably cured may be formed by maintaining the concentration of the shell curing agent atmosphere suitably. The capsules having a cured shell may be recovered by the capsule recovery device 56.

In the second embodiment, the shell is cured in a gas phase, and the capsules are recovered by the capsule recovery device 56. Accordingly, the operation of the recovery process may be simplified, as compared to the case where capsules are recovered from a liquid phase. Furthermore, the management of the number of capsules after completion is facilitated.

Third Embodiment

In an encapsulation device according to a third embodiment of the invention, multilayer capsules are formed by using two or more liquid films.

Figure 11:
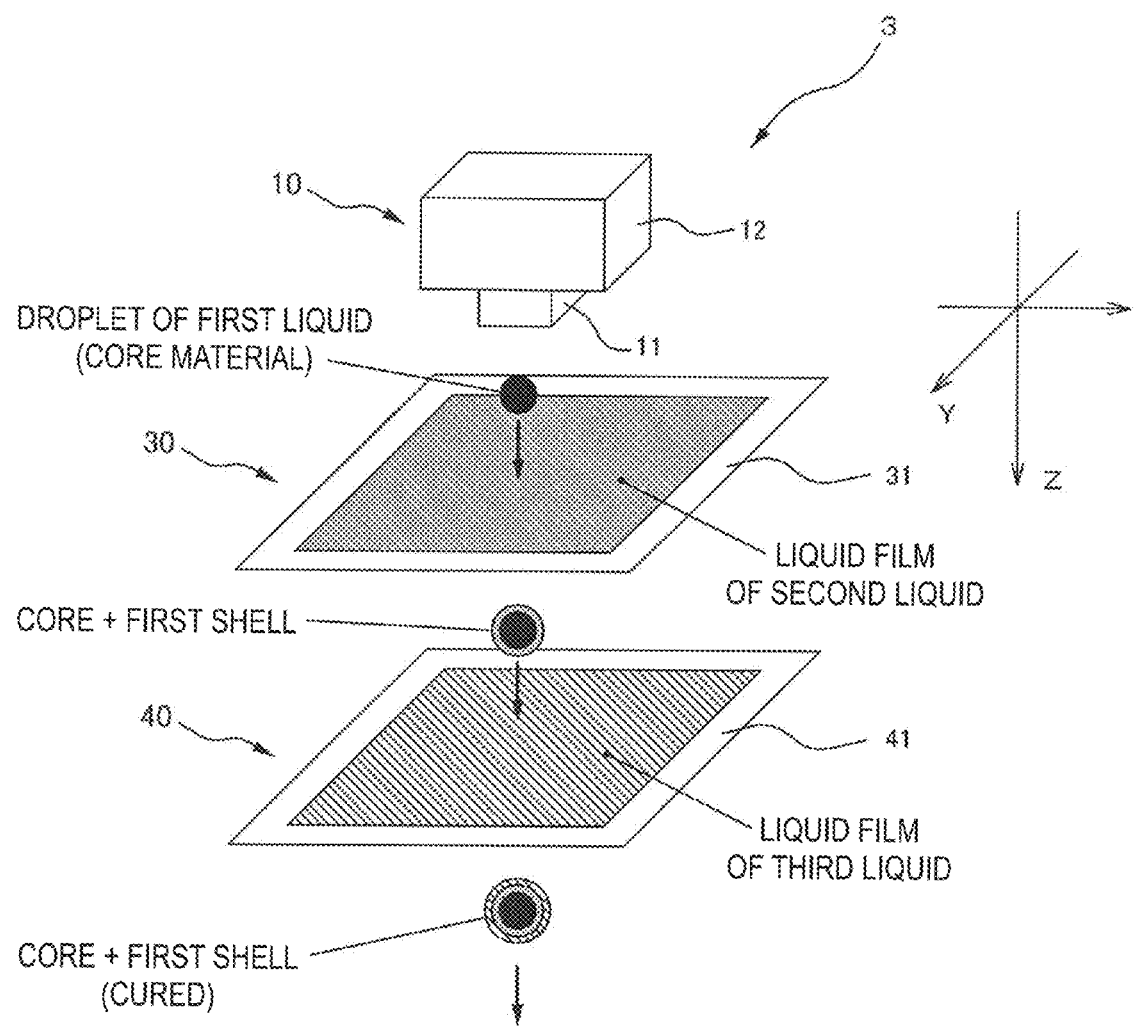
FIG. 11 is a schematic diagram showing a structure of one embodiment of an encapsulation device according to a third embodiment.

FIG. 11 is a schematic diagram showing a structure of one embodiment of an encapsulation device 3 according to the third embodiment. The encapsulation device 3 has a fluid injection device 10, a second liquid holder 30 and a third liquid holder 40. In the encapsulation device 3, the fluid injection device 10 and the second liquid holder 30 are substantially the same as in the encapsulation device 1.

The third liquid holder 40 has substantially the same structure as the second liquid holder 30, and has a liquid film holding frame 41. The liquid film holding frame 41 holds the third liquid in the form of a thin film. The third liquid is surrounded by the liquid film holding flame 41 and thereby forms a liquid film of the third liquid with the liquid film holding frame 41 as an outer edge.

The materials for forming capsules are the same as in the first embodiment. The first liquid is used as a core material, the second liquid is used as a shell material, and the third liquid is used as a shell curing agent. In the third embodiment, the third liquid holder 40 has a part of the function of the liquid contact device in the first embodiment.

Capsule Formation Process

The capsule formation process in the third embodiment is substantially the same as that in the first embodiment (FIG. 5), but the shell curing is different from the first embodiment.

In the shell curing in the third embodiment, the two-phase droplet having been passed through the liquid film of the second liquid is passed through the liquid film of the shell curing agent (the third liquid), thereby wrapping the shell with the shell curing agent. Thus, the shell material (the second liquid) is made in contact with the shell curing agent (the third liquid) to induce chemical reaction, thereby curing the shell. For example, a sodium alginate aqueous solution (the second liquid) is made in contact with a calcium chloride aqueous solution (the third liquid) to induce crosslinking reaction, thereby curing the sodium alginate aqueous solution (the second liquid) through gelation.

The thickness and the hardness of the shell thus formed may be controlled by changing the conditions upon passing the two-phase droplet through the liquid film of the shell curing agent (the third liquid). For example, the amount of the shell curing agent wrapping the shell may be controlled by changing the thickness of the liquid film of the shell curing agent. When the thickness of the liquid film of the shell curing agent is decreased, the amount of the shell curing agent wrapping the shell is decreased, and thereby the number of calcium ions participating in the crosslinking reaction is decreased. Accordingly, the crosslinking reaction proceeds in the surface of the shell, but is hard to proceed in the interior of the shell, thereby thinning the cured portion of the shell. When the thickness of the liquid film of the shell curing agent is increased, on the other hand, the amount of the shell curing agent wrapping the shell is increased to facilitate progress of the crosslinking reaction, thereby thickening the cured portion of the shell.

Capsules capable of being adapted to various applications may be formed by controlling arbitrarily the thickness and the hardness of the shell. For example, in the case where the capsules are applied to a medical field, the period of time from the ingestion of the capsules by human bodies to the exposure of the core through breakage of the shell may be controlled by changing the strength (hardness) of the shell. Accordingly, the capsules may be applied to DDS described above.

Fourth Embodiment

In a fourth embodiment, multilayer capsules having plural shells are formed. An encapsulation device 4 according to the fourth embodiment capable of forming capsules having a core, a first shell and a second shell shown in FIG. 1B will be described.

Figure 12:
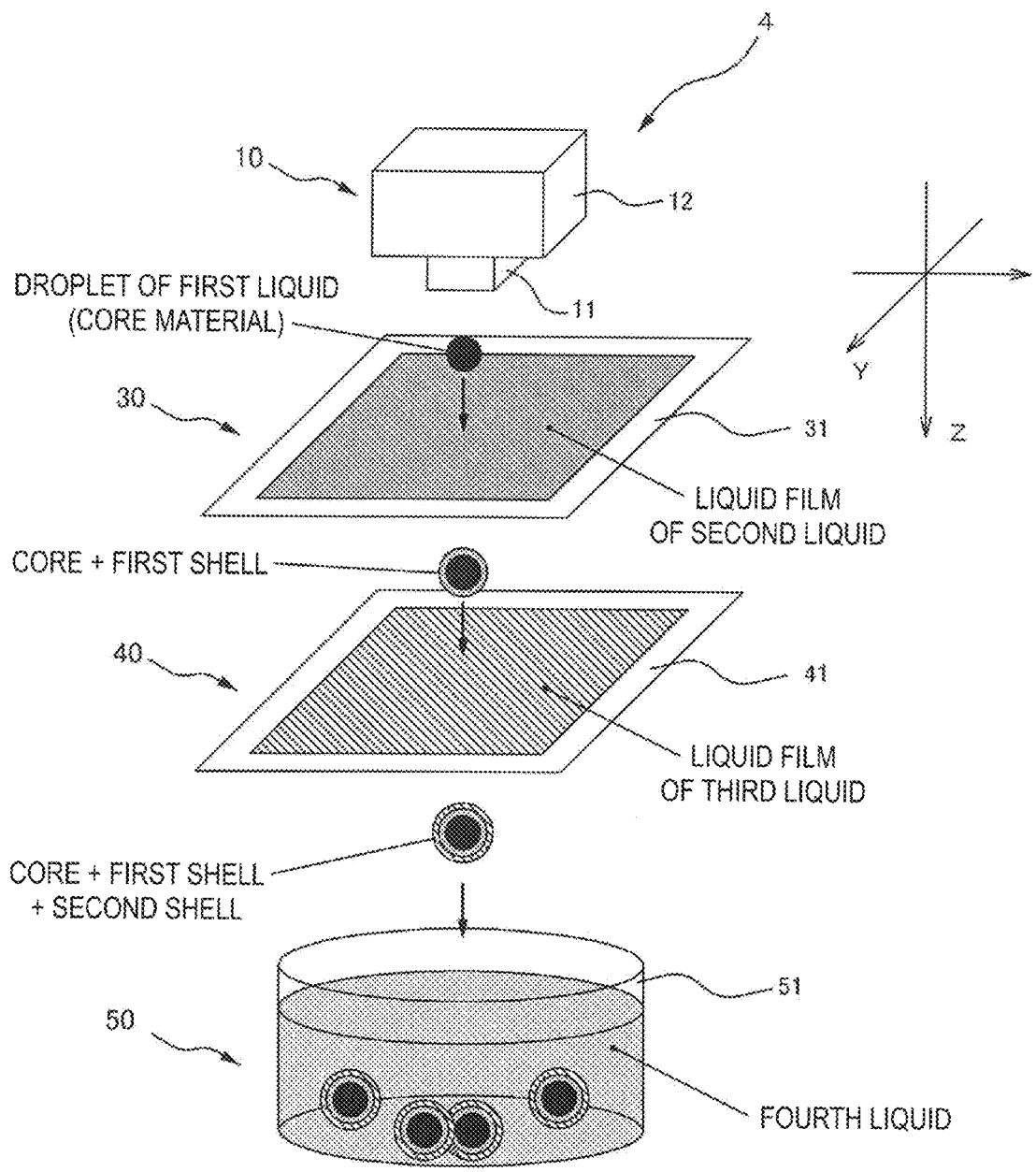
FIG. 12 is a schematic diagram showing a structure of one embodiment of an encapsulation device according to a fourth embodiment.

FIG. 12 is a schematic diagram showing a structure of one embodiment of the encapsulation device 4 according to the fourth embodiment. The encapsulation device 4 has a fluid injection device 10, a second liquid holder 30, a third liquid holder 40 and a liquid contact device 50. In the encapsulation device 4, the fluid injection device 10 and the second liquid holder 30 are substantially the same as in the encapsulation device 1.

The third liquid holder 40 has substantially the same structure as the second liquid holder 30, and holds a third liquid in the form of a thin film with a liquid film holding frame 41.

The liquid contact device 50 has substantially the same structure as the liquid contact device 50 in the first embodiment, and stores a fourth liquid in the form of liquid in a liquid reservoir tank 51.

In the fourth embodiment, the first liquid is a core material, and for example, an aqueous solution containing an active ingredient, such as a drug solution, may be used as the first liquid.

The second liquid is a first shell material for forming a first shell, and for example, a substance that is less miscible with the first liquid and the third liquid may be used.

The third liquid is a second shell material for forming a second shell, and for example, an aqueous solution containing a polysaccharide or a protein may be used.

The fourth liquid is a shell curing agent for curing the second shell, and for example, an aqueous solution containing a polyvalent metal salt having a gelation inducing factor may be used.

Capsule Formation Process

Figure 13:
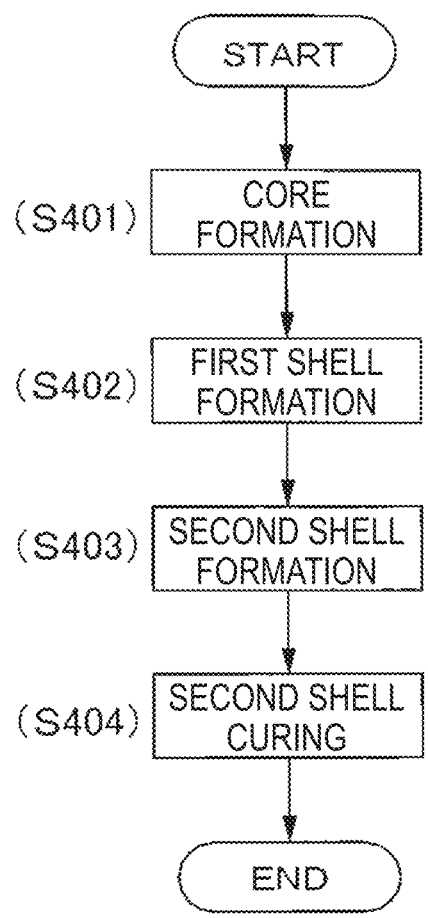
FIG. 13 is a flow chart showing a capsule formation process according to the fourth embodiment.

FIG. 13 is a flow chart showing a capsule formation process according to the fourth embodiment.

In FIG. 13, core formation (S401) and first shell formation (S402) are substantially the same as the core formation (S101) and the shell formation (S102) in FIG. 5, respectively. A core is formed with a droplet of the core material (the first liquid) (S401), and the core is wrapped with the first shell material (the second liquid) to form the first shell (S402), thereby forming a two-phase droplet.

The two-phase droplet having been passed through the liquid film of the second liquid then enters a liquid film of the second shell material (the third liquid). Upon passing through the liquid film, the first shell is wrapped with the second shell material to form the second shell (S403), thereby forming a three-phase droplet. Materials that are less miscible with each other may be selected as the first shell material (the second liquid) and the second shell material (the third liquid), thereby preventing bleeding or the like between the first shell and the second shell from occurring.

The three-phase droplet having been passed through the liquid film of the third liquid and having the second shell wrapping the core and the first shell then enters directly the liquid reservoir tank 51. The shell curing agent (the fourth liquid) stored in the liquid reservoir tank 51 is made in contact with the second shell (the third liquid) to induce chemical reaction, thereby curing the second shell (S404).

The capsules having the cured second shell are recovered by the recovery mechanism of the liquid contact device 50. Consequently, multilayer capsules having two shells are formed.

Fifth Embodiment

In a fifth embodiment, multilayer capsules having much functions are formed by using three or more liquid films.

Figure 14:
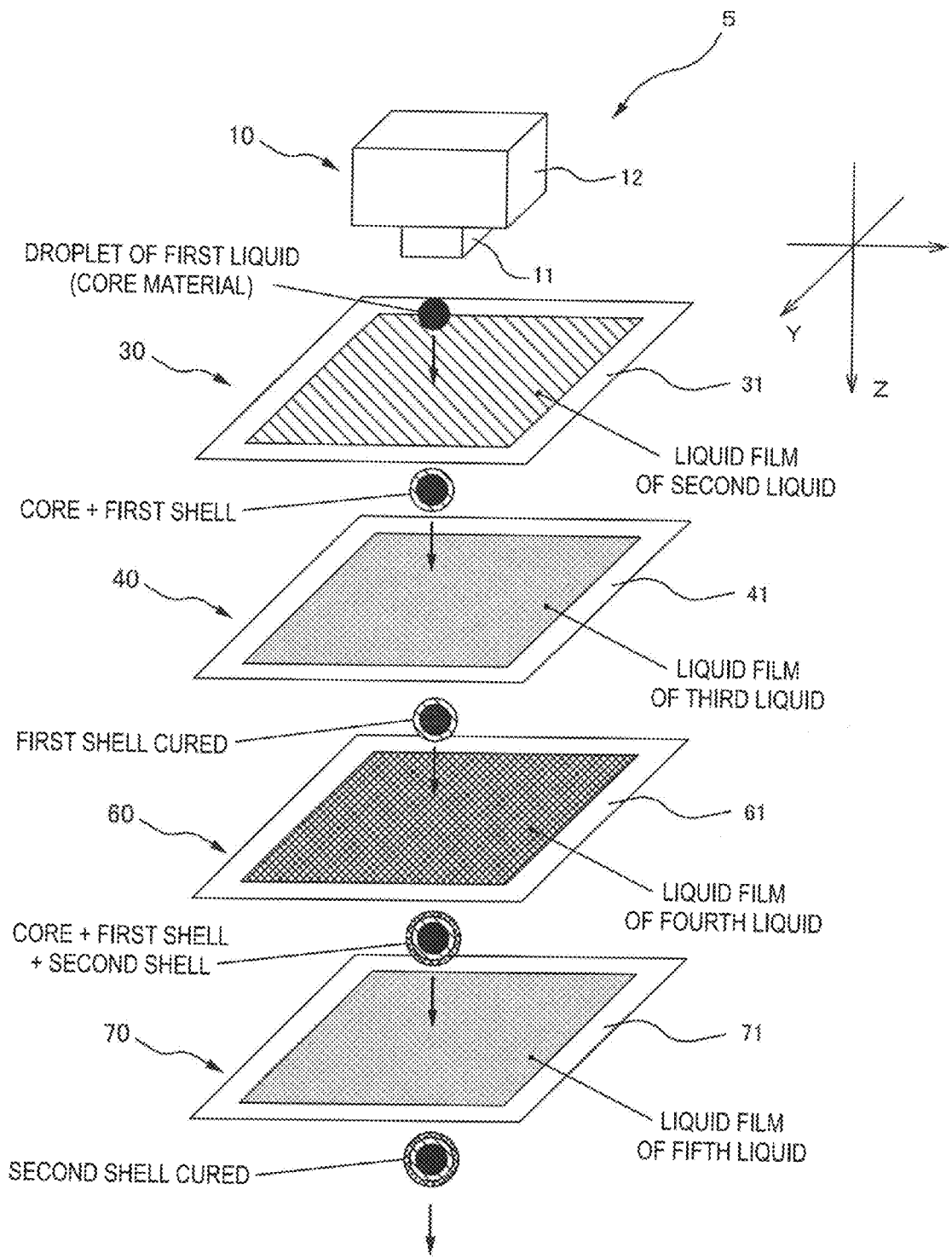
FIG. 14 is a schematic diagram showing a structure of one embodiment of an encapsulation device according to a fifth embodiment.

FIG. 14 is a schematic diagram showing a structure of one embodiment of an encapsulation device 5 according to the fifth embodiment. The encapsulation device 5 has a fluid injection device 10, a second liquid holder 30, a third liquid holder 40, a fourth liquid holder 60 and a fifth liquid holder 70.

The fluid injection device 10 has substantially the same structure as the fluid injection device 10 of the encapsulation device 1. The first liquid is a core material, and for example, an aqueous solution containing an active ingredient may be used.

The second to fifth liquid holders each have substantially the same structure as the second liquid holder 30 of the encapsulation device 1.

The second liquid holder 30 holds a liquid film of the second liquid. The second liquid is a first shell material for forming a first shell, and for example, an aqueous solution containing a polysaccharide or a protein may be used.

The third liquid holder 40 holds a liquid film of the third liquid. The third liquid is a first shell curing agent for curing the first shell, and for example, an aqueous solution containing a polyvalent metal salt having a gelation inducing factor may be used.

The fourth liquid holder 60 holds a liquid film of the fourth liquid. The fourth liquid is a second shell material for forming a second shell, and for example, an aqueous solution containing a polysaccharide or a protein may be used.

The fifth liquid holder 70 holds a liquid film of the fifth liquid. The fifth liquid is a second shell curing agent for curing the second shell, and for example, an aqueous solution containing a polyvalent metal salt having a gelation inducing factor may be used.

Capsule Formation Process

Figure 15:
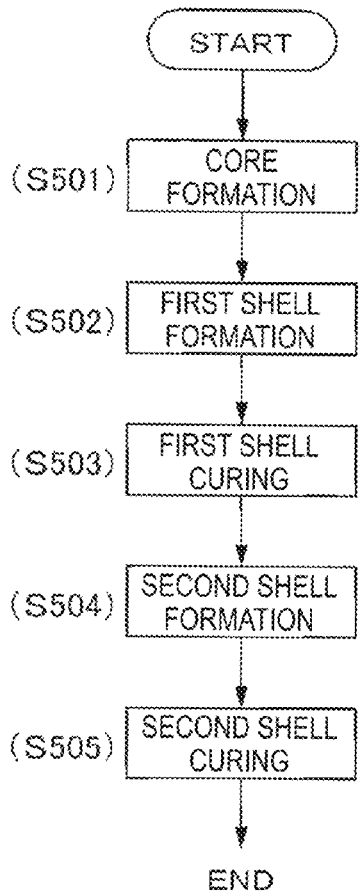
FIG. 15 is a flow chart showing a capsule formation process according to the fifth embodiment.

FIG. 15 is a flow chart showing a capsule formation process according to the fifth embodiment.

Firstly, a core is formed with a droplet of the core material (the first liquid) (S501). The core thus formed enters a liquid film of the first shell material (the second liquid), and is passed through the liquid film, thereby wrapping the core with the first shell material to form a first shell (S502).

The core wrapped with the first shell enters a liquid film of the first shell curing agent (the third liquid). Upon passing through the liquid film, the core wrapped with the first shell is wrapped with the first shell curing agent, and the first shell material (the second liquid) is made in contact with the first shell curing agent (the third liquid) to induce chemical reaction, thereby curing the first shell (S503) and forming a two-layer capsule.

The capsule having the cured first shell then enters a liquid film of the second shell material (the fourth liquid). Upon passing through the liquid film, the capsule is wrapped with the second shell material and a second shell is formed and accumulated on the first shell (S504). No bleeding occurs between the first shell and the second shell since the first shell has been cured. Accordingly, the ranges may be further enhanced, from which the liquid materials used as the first shell material (the second liquid) and the second shell material (the fourth liquid) are selected. For example, aqueous materials may be selected for both the first shell material and the second shell material, i.e., the restrictions on the liquid materials used for accumulating the shells may be reduced, and therefore, a wide variety of liquid materials may be used.

The capsule having the second shell formed then enters a liquid film of the second shell curing agent (the fifth liquid). Upon passing through the liquid film, the capsule having the second shell is wrapped with the second shell curing agent, and the second shell material (the fourth liquid) is made in contact with the second shell curing agent (the fifth liquid) to induce chemical reaction, thereby curing the second shell (S505).

Consequently, a multilayer capsule having two cured shell accumulated is formed.

In the case where a multilayer capsule having three or more shells is formed, the numbers of the liquid films of the shell materials and the shell curing agents are increased, and the shell formation and the shell curing (e.g., S504 and S505) are repeatedly performed. The plural shells may be imparted with different functions, thereby forming capsules having various functions depending on the purposes thereof.

Figure 16:
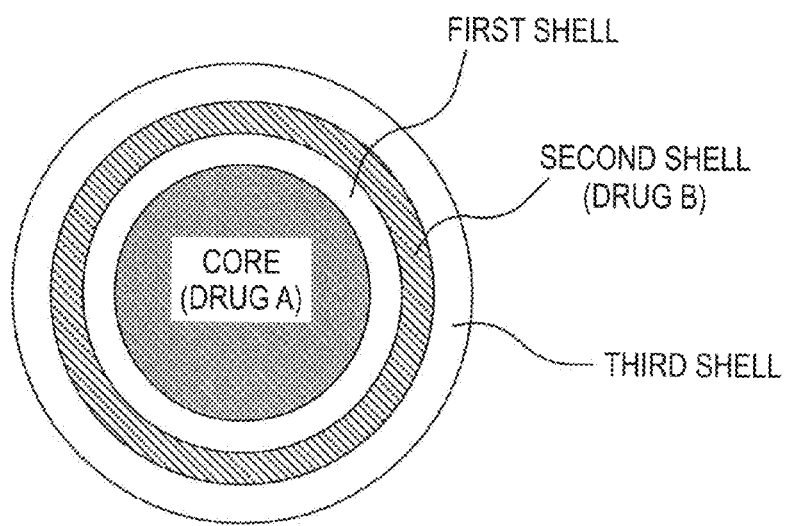
FIG. 16 is a schematic diagram showing an example of a capsule having three shells.

FIG. 16 is a schematic diagram showing an example of a capsule having three shells. In the example shown in FIG. 16, the core is formed of a drug effective for the small intestine (drug A), the first shell is formed of a substance that is not dissolved in the gastric acid, the second shell is formed of a drug effective for the stomach (drug B), and the third shell is formed of a substance that is dissolved in the gastric acid.

Upon ingestion of the capsules by a human, the third shell is dissolved by the action of the gastric acid in the stomach, and the second shell (drug B) is released. The first shell is not dissolved in the gastric acid, and therefore, the core is not released in the stomach. Subsequently, at such a timing that the capsules reach the small intestine, the first shell is broken by such measures as ultrasonic waves applied externally, thereby releasing the core (drug A) in the small intestine. In the capsule shown in FIG. 16, the core and the second shell have functions as a drug, and the first shell and the third shell have function of protecting the drugs. The core and the shells are imparted with different functions, and thereby capsules capable of being adapted to plural purposes by a single kind of capsules may be formed.

As another example, good bacteria, such as bifidobacteria and *Lactobacillus gasseri*, or *lactobacillus* are enclosed alive in the core of the multilayer capsule, and the shell is formed with a substance that is hard to be dissolved in the gastric acid. The use of the capsules mixed in foods, such as yoghurt, facilitates arrival of good bacteria alive at the intestine. Furthermore, various functions may be combined by selecting properly the materials for forming the capsules and the size of the capsules, and thus the capsules have a wide variety of applications as functional foods.

Modified Embodiment

In the embodiment shown in FIG. 14, capsules are formed by using the second liquid and the fourth liquid as the shell materials and the third liquid and the fifth liquid as the shell curing agents, and as modified embodiments, various kinds of capsules may be formed by changing the kinds of the liquids held as the liquid films in the encapsulation device 5. For example, shell materials are used as the second to fourth liquids, and a shell curing agent is used as the fifth liquid, thereby forming capsules where only the outermost shell is cured.

Proper selection of the kinds and properties of the liquids held as the liquid films facilitates formation of multilayer capsules having intended functions.

Sixth Embodiment

In a sixth embodiment, capsules are formed by curing a shell by irradiating of ultraviolet ray.

Figure 17:
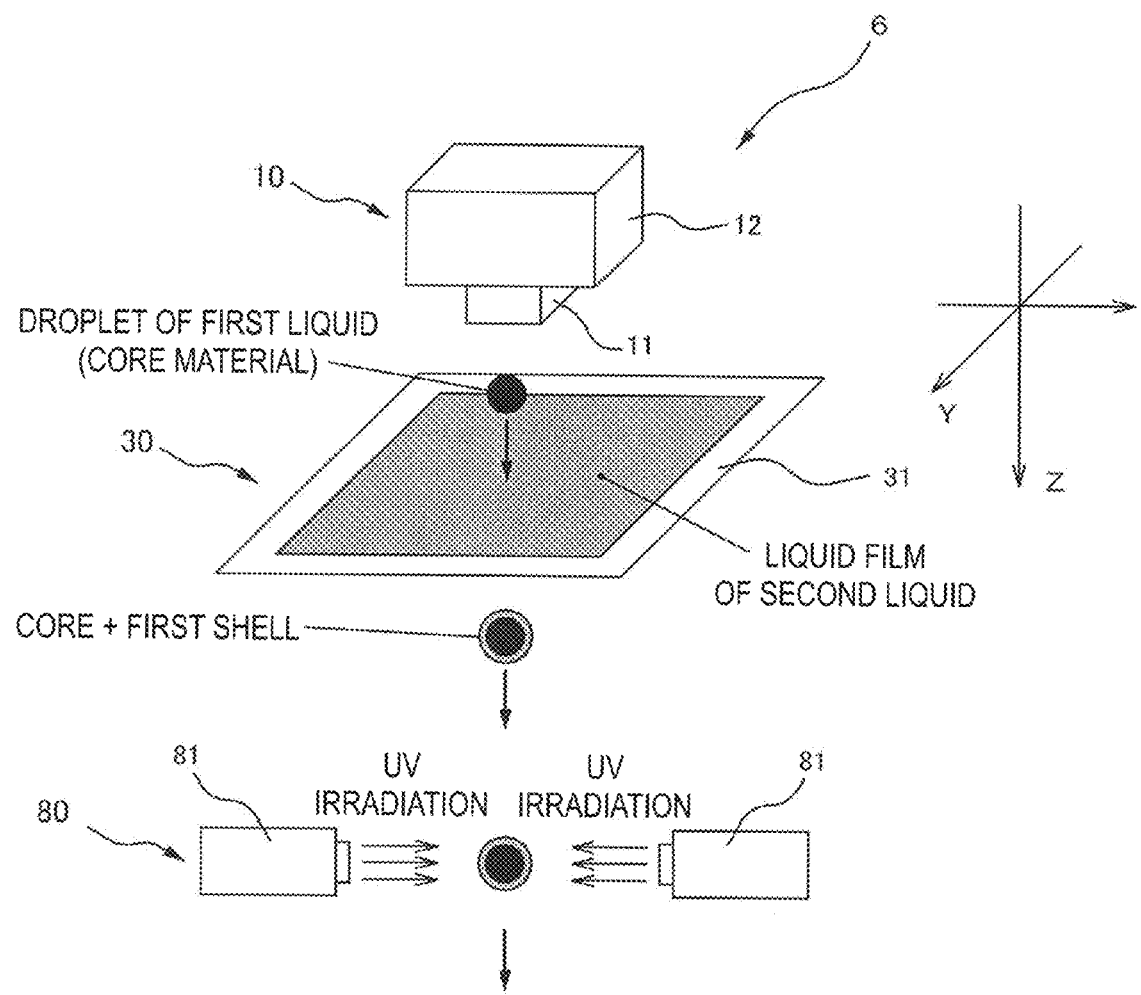
FIG. 17 is a schematic diagram showing a structure of one embodiment of an encapsulation device according to a sixth embodiment.

FIG. 17 is a schematic diagram showing a structure of one embodiment of an encapsulation device 6 according to the sixth embodiment. The encapsulation device 6 has a fluid injection device 10, a second liquid holder 30 and a light irradiation device 80. In the encapsulation device 6, the fluid injection device 10 and the second liquid holder 30 are substantially the same as in the encapsulation device 1.

The light irradiation device 80 has an UV irradiation device 81. The UV irradiation device 81 is an irradiator capable of radiating UV ray (ultraviolet ray), and has, for example, a light emitting diode (LED) as an UV light source. The UV irradiation device 81 is disposed below the second liquid holder 30, and radiates UV ray to the two-phase droplets having been passed through the liquid film of the second liquid. Two UV irradiation devices 81 are provided in the embodiment shown in FIG. 17, but the number of the UV irradiation devices 81 and the positions where they are disposed may be adjusted depending on the necessary UV irradiation dose. The liquid film of the second liquid is prevented from being irradiated.

The light irradiation device 80 may radiate other electromagnetic waves than UV ray.

Materials of Capsules

In the sixth embodiment, a liquid containing an effective ingredient may be used as the first liquid, as similar to the aforementioned embodiments, and a liquid capable of being cured through irradiation of light, such as UV ray (which may be hereinafter referred to as an UV curing material) is used as the second liquid (the shell material).

The UV curing material may contain a polymerizable compound and a photopolymerization initiator. The polymerizable compound is a compound that undergoes polymerization reaction upon irradiation with light. Specific examples of the polymerizable compound include various acrylate monomers, various acrylate oligomers, various vinyl monomers and various vinyl ether monomers. The photopolymerization initiator is a catalyst having a function of initiating efficiently polymerization of the polymerizable compound upon irradiation of light. Upon irradiating the UV curing material with UV ray, the photopolymerization initiator is activated to form reaction initiating points. The reaction initiating points activate double bonds of the oligomers or the like, and the oligomers are bonded to each other and finally polymerized in the form of a network, thereby changing the UV curing material from liquid to solid.

Capsule Formation Process

The capsule formation process in the sixth embodiment is substantially the same as in the first embodiment (FIG. 5), but the shell curing is different. In the sixth embodiment, the shell is imparted with suitable hardness through irradiation of UV ray.

In the shell curing in the sixth embodiment, the two-phase droplet having been passed through the liquid film of the second liquid is irradiated with UV ray from the light irradiation device 80 in the course of migration of the droplet in the migration direction thereof. Upon irradiation of UV ray, photopolymerization reaction proceeds in the surface of the shell (the second liquid), and the shell is cured, thereby forming a capsule.

The hardness of the shell may be controlled by changing the irradiation dose of UV ray. For example, in the case where a hard shell is to be formed, the irradiation energy of the UV irradiation device 81 may be increased, or the number of the UV irradiation device 81 may be increased. When the total irradiation dose of UV ray radiated is increased, the photopolymerization reaction may sufficiently proceed throughout the surface and the interior of the shell, thereby hardening the shell.

Other Embodiments

The encapsulation devices according to some aspects of the invention have been described with reference to some embodiments above, and the embodiments are shown only for facilitating understanding of the invention but do not limit the invention. The invention may be modified and improved without deviating from the invention, and includes any equivalent of the invention. Embodiments shown below are also included in the invention.

Capsule Formation Materials

While the first to fifth liquids have been described with reference to specific examples in the aforementioned embodiments, other capsule formation materials than those described above may be used for forming capsules.

Disposition of Devices

While the fluid injection device, the liquid films and the liquid contact device are disposed linearly in the vertical direction in the aforementioned embodiments, the disposition of the devices are not limited thereto. For example, in the case where the core is injected from the fluid injection device in an oblique direction with respect to the vertical direction, the devices may be disposed in the migration direction of the core.

Application to EPD

The microcapsules (the multilayer capsules) formed in the aforementioned embodiments may be applied to EPD (electrophoretic display), which is one of display methods with electronic ink.

In EPD, plural microcapsules are spread over a film and arranged in the form of a matrix. The microcapsules are each filled with a liquid, and the liquid contains a large number of black and white fine particles floating therein. Upon applying an electric field to the microcapsules arranged on the film, the black and white fine particles can be moved within the microcapsules. For example, in the case where the white fine particles are positively charged and the black fine particles are negatively charged, the white fine particles are moved upward within the microcapsules upon applying a negative electric charge from the upper side of the microcapsules, and the surface of the film appears white. According to the mechanism, black-and-white patterns may be expressed on the surface of the film.

In the aforementioned embodiments, the first liquid (the core material) containing white fine particles and black fine particles dispersed therein is injected to form a core. Thereafter, the core is passed through a liquid film of the second liquid (the shell material) to form a shell wrapping the core, thereby forming easily multilayer capsules for EPD containing the white and black fine particles floating inside the core. The capsules have a wide applicability to EPD, for example, the shell may be colored to form capsules with different colors.

Examples of liquids as raw materials for forming the multilayer capsules for EPD are shown below.

Examples of the first liquid (the core material), in which the fine particles are dispersed, include xylene, toluene, liquid paraffin, a silicone oil, a chlorinated organic compound, various hydrocarbons and various aromatic hydrocarbons. Examples of the white fine particles include titanium oxide, alumina particles and zinc oxide. Examples of the black fine particles include carbon black.

Examples of the second liquid (the shell material) include liquid materials described for the aforementioned embodiments. Examples of the third liquid (the shell curing agent) include liquid materials described for the aforementioned embodiments.

This application claims priority to Japanese Patent Application No. 2011-213190 filed on Sep. 28, 2011, Japanese Patent Application No. 2011-213192 filed on Sep. 28, 2011, and Japanese Patent Application No. 2012-117887 filed on May 23, 2012, the entirety of all of which is hereby incorporated by reference.

What is claimed is:

1. A drug encapsulation device configured to form drug containing capsules of under 100 microns in diameter, the drug encapsulation device comprising:
    a liquid injection device that injects a first liquid to form a core;
    a liquid film holder that holds a second liquid in film form, wherein a shell of the second liquid containing the core is formed when the core passes through the second liquid wherein at least one of the first liquid and the second liquid comprises a drug; and
    a fluid contact device that makes the shell come into contact with a third liquid,
    wherein the first liquid is injected toward a liquid film of the second liquid retained by the liquid film holder,
    wherein the core is wrapped with the second liquid on passing through the liquid film of the second liquid,
    wherein a chemical reaction is induced in the shell when the shell is in contact with the third liquid;
    a distance from the fluid injection device to a surface of the liquid film of the liquid film holder is from 10 to 10,000 μm; and
    wherein a distance from the surface of the liquid film of the liquid film holder to a liquid surface of the fluid contact device is from 0.1 to 50 mm.

2. The drug encapsulation device according to claim 1, wherein
    the fluid contact device includes a liquid reservoir that reserves the third liquid in liquid form, and
    wherein the second liquid wrapped around the core is made to come into contact with the third liquid when the second liquid enters the liquid reservoir.

3. The drug encapsulation device according to claim 1, wherein
    the fluid contact device has a mist generator that mists the third liquid in mist form, and
    the second liquid is made in contact with the third liquid by misting the third liquid from the mist generator to an area, toward which the core wrapped with the second liquid is moved.

4. The drug encapsulation device according to claim 2, wherein
    the second liquid is an aqueous solution containing a polysaccharide or a protein, and
    the third liquid is an aqueous solution containing a polyvalent metal salt.

5. The drug encapsulation device according to claim 1, wherein
    the liquid injection device has a nozzle that injects droplets of the first liquid, and a device that is driven by an electric voltage signal to make the droplets to be injected from the nozzle, and
    a size of the droplets injected from the liquid injection device is controlled by changing a voltage of the electric voltage signal.

6. The drug encapsulation device according to claim 5, wherein
    the liquid injection device has a plurality of the nozzles, and
    the droplets are injected from the plurality of the nozzles.

7. A drug encapsulation method to form drug containing capsules of under 100 microns, the method comprising:
    forming a core by injecting a first liquid toward a liquid film of a second liquid retained in film form;
    wrapping the core with the second liquid by passing the core through the liquid film of the second liquid, thereby forming a shell containing the core; and
    making the shell come into contact with a third liquid to induce a chemical reaction; and
    controlling a contact time between the core and the second liquid and a contact time between the shell and the third liquid.

8. The drug encapsulation device of claim 1, further comprising:
    a third liquid holder that holds in film form the third liquid, wherein
    the droplets wrapped with the second liquid are passed through the liquid film of the third liquid held by the third liquid holder, thereby wrapping the droplets wrapped with the second liquid with the third liquid.

* * * * *